(12) United States Patent
Schmieding

(10) Patent No.: US 12,702,401 B2
(45) Date of Patent: Aug. 11, 2026

(54) SURGICAL CONSTRUCTS FOR TISSUE FIXATION AND METHODS OF TISSUE REPAIRS

(71) Applicant: Arthrex, Inc., Naples, FL (US)

(72) Inventor: John W. Schmieding, Naples, FL (US)

(73) Assignee: ARTHREX, INC., Naples, FL (US)

( * ) Notice: Subject to any disclaimer, the term of this patent is extended or adjusted under 35 U.S.C. 154(b) by 1035 days.

(21) Appl. No.: 17/065,882

(22) Filed: Oct. 8, 2020

(65) Prior Publication Data

US 2021/0100547 A1 Apr. 8, 2021

Related U.S. Application Data

(63) Continuation-in-part of application No. 16/593,057, filed on Oct. 4, 2019, now Pat. No. 11,576,666.

(51) Int. Cl.

*A61B 17/04* (2006.01)
*A61B 17/06* (2006.01)
(Continued)

(52) U.S. Cl.

CPC .. *A61B 17/0466* (2013.01); *A61B 2017/0464* (2013.01); *A61B 2017/0496* (2013.01);
(Continued)

(58) Field of Classification Search

CPC ............ A61B 17/0401; A61B 17/0466; A61B 17/0485; A61B 17/06166;
(Continued)

(56) References Cited

U.S. PATENT DOCUMENTS 1,054,014 A 2/1913 Mcfadden
1,239,433 A 9/1917 Reed
(Continued)

FOREIGN PATENT DOCUMENTS

EP 0744165 A1 11/1996
EP 2455002 A1 5/2012
(Continued)

OTHER PUBLICATIONS

References Are Not Being Filed Herewith. They Are Already of Record in One or More of the Following Applications, Which Are Being Relied on for Priority Under 35 U.S.C. Section 120 (see 37 C.F.R. Section 1.98(d)(1)): U.S. Appl. No. 16/593,057, filed Oct. 4, 2019.

(Continued)

*Primary Examiner* — Diane D Yabut
*Assistant Examiner* — Christian D Knauss
(74) *Attorney, Agent, or Firm* — Potomac Law Group, PLLC

(57) ABSTRACT

Surgical constructs, assemblies and methods of tissue fixation are disclosed. A surgical construct includes a spreadable web attached to a plurality of peripheral strands. The spreadable web may be tensionable and may include one or more flexible filaments or strands. At least one of the filaments is coupled to the peripheral strands. The filaments may extend from the peripheral strands in different directions and/or orientations. The spreadable web is expandable and can be adjusted to various widths. The spreadable web may be knotless. The spreadable web may be tensionable. The surgical construct may be attached to one or more knotted or knotless fixation devices.

16 Claims, 13 Drawing Sheets

(51) Int. Cl.
*A61F 2/08* (2006.01)
*A61F 2/40* (2006.01)

(52) U.S. Cl.
CPC ................ *A61B 2017/0618* (2013.01); *A61F 2002/0852* (2013.01); *A61F 2/40* (2013.01)

(58) Field of Classification Search
CPC .... A61B 2017/0427; A61B 2017/0458; A61B 2017/0464; A61B 2017/06185; A61B 2017/081; A61B 2017/086; A61B 2017/088; A61F 2/0811; A61F 2002/0852
See application file for complete search history.

(56) References Cited

U.S. PATENT DOCUMENTS 3,073,303 A 1/1963 Schaar
3,085,572 A 4/1963 Blackford
3,387,345 A 6/1968 Jean-Claude
4,034,763 A 7/1977 Frazier
4,141,363 A 2/1979 James et al.
4,440,171 A 4/1984 Nomoto et al.
4,604,821 A 8/1986 Moser
4,962,757 A 10/1990 Stefan
5,520,021 A 5/1996 Clerici
5,628,756 A 5/1997 Barker, Jr. et al.
5,664,441 A 9/1997 Clerici
5,669,935 A 9/1997 Rosenman et al.
5,755,728 A 5/1998 Maki
5,792,181 A 8/1998 Haase et al.
5,968,077 A 10/1999 Wojciechowicz et al.
5,984,933 A 11/1999 Yoon
6,264,675 B1 7/2001 Brotz
6,355,065 B1 3/2002 Gabbay
6,478,727 B2 11/2002 Scetbon
6,589,161 B2 7/2003 Corcoran
6,632,239 B2 10/2003 Snyder et al.
6,726,706 B2 4/2004 Dominguez
7,329,272 B2 2/2008 Burkhart et al.
7,547,316 B2 6/2009 Priewe et al.
7,740,646 B2 6/2010 Hunt et al.
7,815,562 B2 10/2010 Chu
7,892,256 B2 2/2011 Grafton et al.
8,062,363 B2 11/2011 Hirpara et al.
8,123,884 B2 2/2012 Kujawski et al.
8,512,373 B2 8/2013 Gilson et al.
8,562,645 B2 10/2013 Stone et al.
8,690,960 B2 4/2014 Hotter et al.
8,834,521 B2 9/2014 Pinto et al.
8,876,900 B2 11/2014 Guederian et al.
8,951,271 B2 2/2015 Mueller et al.
8,951,287 B1 2/2015 Green et al.
9,066,716 B2 6/2015 Sikora et al.
9,173,645 B2 11/2015 Overes et al.
9,179,950 B2 11/2015 Zajac et al.
9,237,883 B2 1/2016 Sundheimer et al.
9,277,918 B2 3/2016 Gagliano et al.
9,301,745 B2 4/2016 Dreyfuss
9,332,979 B2 5/2016 Sullivan et al.
9,402,620 B2 8/2016 Pilgeram
9,421,008 B2 8/2016 Burkhart et al.
9,463,011 B2 10/2016 Dreyfuss et al.
9,492,200 B2 11/2016 Sikora et al.
9,539,003 B2 1/2017 Stone et al.
9,572,580 B2 2/2017 Sargeant et al.
9,707,069 B2 7/2017 Kumar
9,730,784 B2 8/2017 Hackney et al.
9,743,919 B2 8/2017 Manos et al.
10,610,217 B2 4/2020 Stone et al.
11,065,105 B2 7/2021 Konicek
2003/0096076 A1 5/2003 Allison
2003/0130694 A1 7/2003 Bojarski et al.
2005/0284801 A1* 12/2005 Tacklind ............. A61B 17/085 209/132
2007/0032822 A1 2/2007 Ortiz et al.
2007/0288023 A1* 12/2007 Pellegrino ................. A61F 2/08 606/232
2008/0058867 A1 3/2008 Dean
2008/0082113 A1 4/2008 Bishop et al.
2008/0131659 A1 6/2008 Mueller
2008/0188936 A1* 8/2008 Ball ......................... A61F 2/08 623/13.13
2008/0228219 A1 9/2008 Weiser
2009/0012560 A1 1/2009 Hunter et al.
2009/0054911 A1 2/2009 Mueller et al.
2009/0088798 A1 4/2009 Snyder et al.
2009/0156997 A1 6/2009 Trenhaile
2009/0275962 A1* 11/2009 Zeiner .................. A61F 5/0083 606/151
2009/0318960 A1* 12/2009 Burkhart ............... A61F 2/0811 606/228
2009/0318962 A1 12/2009 Spedden et al.
2009/0318966 A1* 12/2009 Green ................ A61B 17/0642 606/232
2010/0063599 A1 3/2010 Brunelle et al.
2010/0305394 A1 12/2010 Rosenblatt
2011/0040325 A1 2/2011 Moehrle
2011/0137419 A1 6/2011 Wong
2011/0264141 A1 10/2011 Denham et al.
2012/0245602 A1 9/2012 Glick
2012/0245629 A1 9/2012 Gross et al.
2013/0096611 A1 4/2013 Sullivan
2013/0116799 A1 5/2013 Derwin et al.
2014/0067061 A1 3/2014 Kubiak et al.
2014/0094931 A1 4/2014 Derwin et al.
2014/0257384 A1 9/2014 Dreyfuss et al.
2015/0025552 A1 1/2015 Stoll
2015/0066079 A1 3/2015 Schmieding
2015/0313593 A1 11/2015 Patenaude
2015/0335327 A1 11/2015 Ferguson et al.
2017/0055975 A1 3/2017 Thal
2017/0095324 A1 4/2017 Adams et al.
2017/0143551 A1* 5/2017 Coleman .............. A61F 2/0063
2017/0215865 A1 8/2017 Sengun et al.
2017/0290578 A1 10/2017 Thal
2017/0340425 A1 11/2017 Sambusseti
2018/0049734 A1 2/2018 Kam
2020/0178951 A1* 6/2020 Johnson ............ A61B 17/0401
2021/0100546 A1 4/2021 Schmieding

FOREIGN PATENT DOCUMENTS

EP 2774546 A1 9/2014
GB 2351768 A 1/2001
JP 2007330376 A 12/2007
WO 2021066928 A1 4/2021

OTHER PUBLICATIONS

International Search Report and Written Opinion dated Oct. 26, 2020, issued in International Application No. PCT/US2020/043671.
Unknown, "Tape," Merriam-Webster.com Dictionary, 2022, retrieved from: https://www.merriam-webster.com/dictionary/tape, retrieved on May 2022.
International Search Report and Written Opinion for International Application No. PCT/US2024/037116 dated Oct. 10, 2024.

* cited by examiner

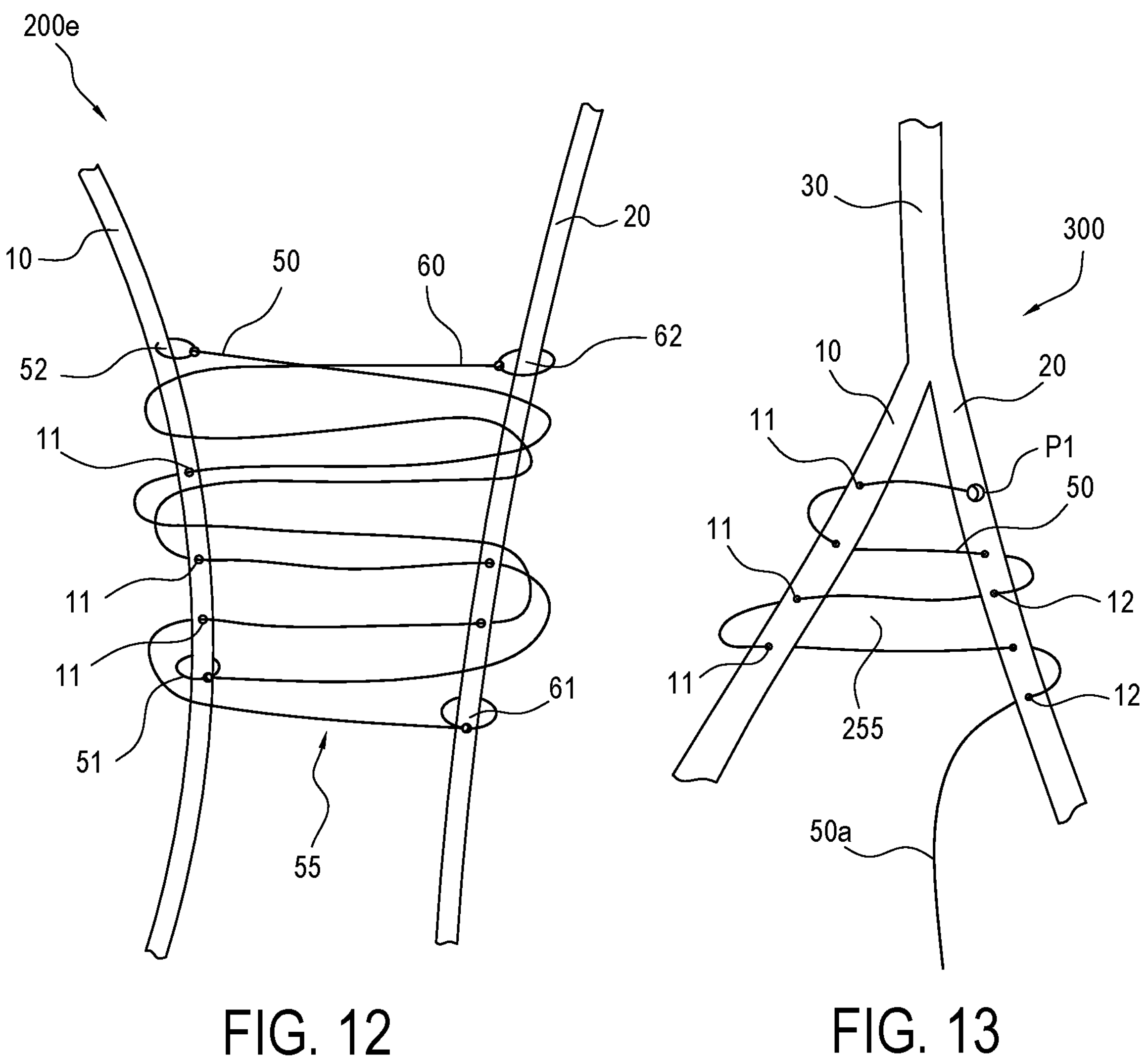
FIG. 12
FIG. 13
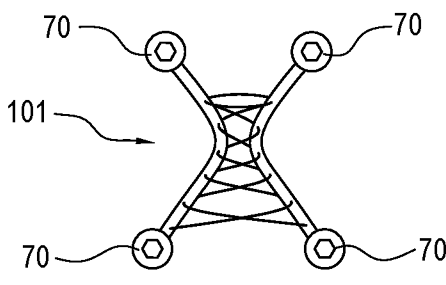
FIG. 14
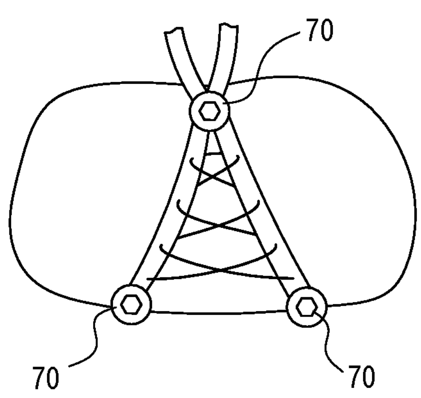
FIG. 15

2
400
1
80
90

400
1
80
55
90
70
70
2

103
1
80
A
B
B
55
90
70
70
2

400
2
2
1
1
80
70
90
70

1
80
55
55
70
70
2
90

1
203
A
A
B
B
B
B
80
55
55
70
70
2
90

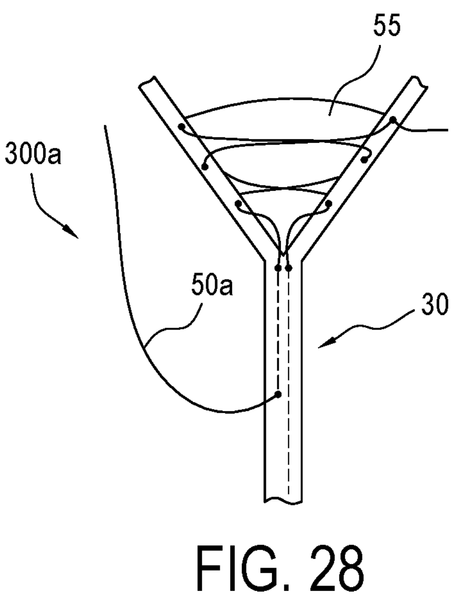
FIG. 28
55
300b
50a
50b
30
FIG. 29
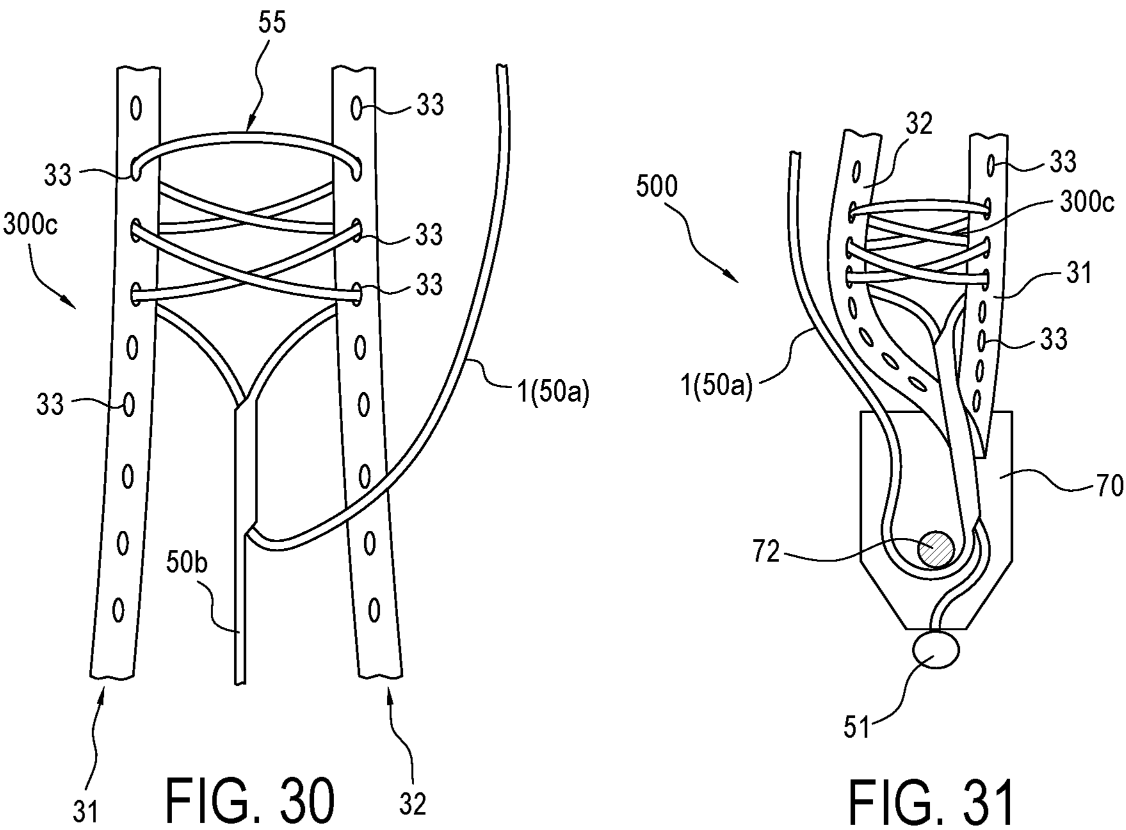
FIG. 30
FIG. 31

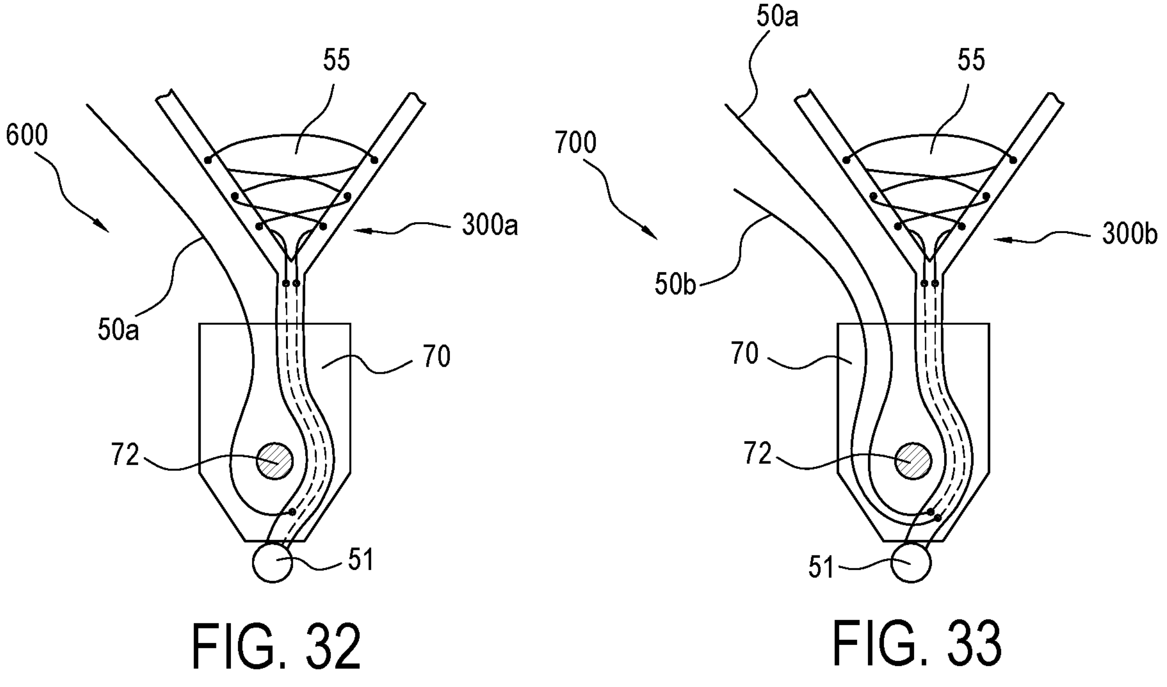
FIG. 32
FIG. 33
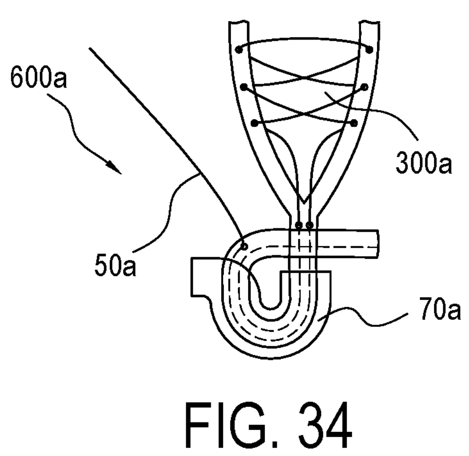
FIG. 34
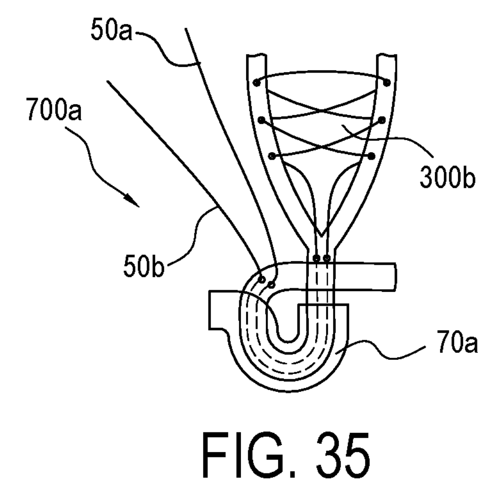
FIG. 35

SURGICAL CONSTRUCTS FOR TISSUE FIXATION AND METHODS OF TISSUE REPAIRS

CROSS-REFERENCE TO RELATED APPLICATIONS

This application is a continuation-in-part of, and claims priority benefit from, U.S. application Ser. No. 16/593,057 filed Oct. 4, 2019, the disclosure of which is incorporated by reference in its entirety herein.

BACKGROUND

The present disclosure relates to the field of surgery and, more particularly, to surgical constructs and methods of tissue repair and fixation.

SUMMARY

Surgical constructs and methods of tissue repairs are disclosed. A surgical construct includes a spreadable web attached to a plurality of peripheral members. The spreadable web may be tensionable and may include one or more flexible filaments or strands. The filaments are coupled to the peripheral members. The filaments may extend in between the peripheral members in different directions and/or orientations. The spreadable web is expandable and can be adjusted to various widths. The spreadable web may be knotless. The spreadable web may be tensionable.

Methods of tissue repairs are also disclosed. A surgical construct provides knotless bridge soft tissue to bone fixation, without knot formation, with fewer passing steps, improved handling through small portals and into the joint space, and increased fixation and uniform soft tissue compression.

BRIEF DESCRIPTION OF THE DRAWINGS

FIG. 12 illustrates another exemplary surgical construct.

FIG. 13 illustrates another exemplary surgical construct.

FIGS. 14 and 15 illustrate schematic exemplary repairs with surgical constructs.

FIGS. 28-35 illustrate schematic views of a surgical construct assembled with knotless fixation devices.

DETAILED DESCRIPTION

Figure 1:
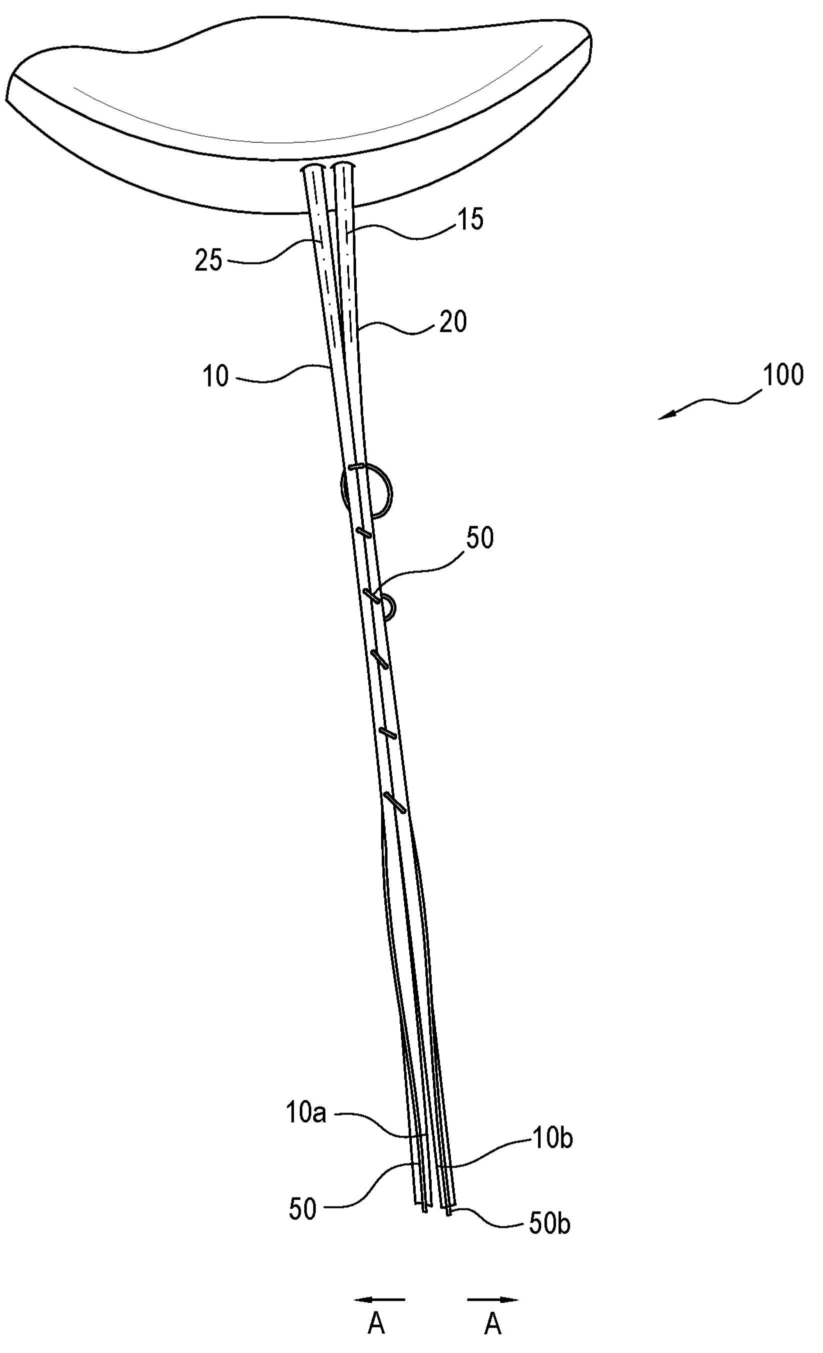
FIG. 1 illustrates an exemplary surgical construct.

The present disclosure provides methods and surgical constructs for fixation of tissue, for example, soft tissue to bone.

A surgical construct includes an expandable spreadable web extending between two peripheral members (support structures, peripheral edges or strands). The expandable spreadable web is formed of at least one flexible filament or strand that is attached to (and/or coupled with) the peripheral members. In an embodiment, the at least one flexible filament or strand is threaded through the peripheral members. In an embodiment, the at least one flexible filament or stand is looped around (wrapped around) the peripheral members. In an embodiment, the at least one flexible filament or strand is both threaded through and looped around the peripheral members. In an embodiment, the at least one flexible filament or strand is fixedly attached to the peripheral members at one or more locations. In an embodiment, none of the flexible strands or filaments is fixedly attached to the peripheral members. The expandable spreadable web travels in at least one direction (dimension) relative to the two peripheral members. The spreadable web is expandable and can be adjusted to various widths.

An exemplary surgical construct is a thin, narrow diameter (narrow width) construct when in a first, unexpanded, undeployed position. In the first position, the exemplary surgical construct is formed of slightly-separated sutures as peripheral members (peripheral edges or support structures) with one or more filaments weaved through at various points. In a second, expanded, deployed position, the peripheral members of the surgical construct are separated so the web (interwebbing) spreads over the area that needs to be compressed and/or approximated. The spreadable web can be adjusted to various widths, such as the desired width to cover (be placed over) the area/tissue of interest.

Methods of knotted or knotless tissue repair are also disclosed. An exemplary method includes inter alia the steps of: (i) securing a surgical construct with a spreadable web and peripheral members to a first tissue; and (ii) positioning the spreadable web over a second tissue and securing the surgical construct. In an exemplary embodiment, the construct includes slightly-separated sutures with a filament weaved through or looped around the slightly-separated sutures (peripheral members) at various points, to form the web. The web is expandable and can be adjusted to various widths.

Referring now to the drawings, where like elements are designated by like reference numerals, FIGS. 1-13 illustrate exemplary surgical constructs 100, 100*a*, 200, 200*a*, 200*b*, 200*c*, 200*d*, 200*e*, 300 (knotless constructs; anchors; knotless anchors; suture web constructs; FiberWeb constructs). FIGS. 14-17 illustrate schematic exemplary repairs with the surgical constructs 100, 100*a*, 200, 200*a*, 200*b*, 200*c*, 200*d*, 200*e*, 300. FIGS. 18-27 illustrate additional schematic exemplary repairs with the surgical constructs 100, 100*a*, 200, 200*a*, 200*b*, 200*c*, 200*d*, 200*e*, 300. FIGS. 28-35 illustrate schematic views of surgical constructs of the disclosure assembled with exemplary knotless fixation devices.

As detailed below with reference to various embodiments, surgical constructs 100, 100*a*, 200, 200*a*, 200*b*, 200*c*, 200*d*, 200*e*, 300 include one or more peripheral members 10, 20, 30 (peripheral edges; peripheral structures; peripheral sutures or tapes; support structures or members; slightly-separated members; slightly-separated sutures) coupled to one or more flexible filaments 50, 60 (strands or flexible couplers 50, 60; inner filaments 50, 60). Exemplary constructs of the present disclosure may include various combinations of peripheral members coupled with filaments, for example: two support members and one filament; two support members and two or more filaments; two or more support members and two or more filaments; a single strand that bifurcates or trifurcates or furcates into multiple support limbs and one filament; a single strand that bifurcates or trifurcates or furcates into multiple support limbs and two or more filaments; two or more strands that bifurcate or trifurcate or furcate (at least one of the strands or any combination of the strands) into multiple support limbs and two or more filaments, among many others. The one por more filaments may be threaded through and/or looped around the support members (for example, threaded at least once through one or more support members and then looped around one or more support members). Thus, the embodiments below are only exemplary and the present disclosure is not limited to the aspects detailed below.

Figure 2:
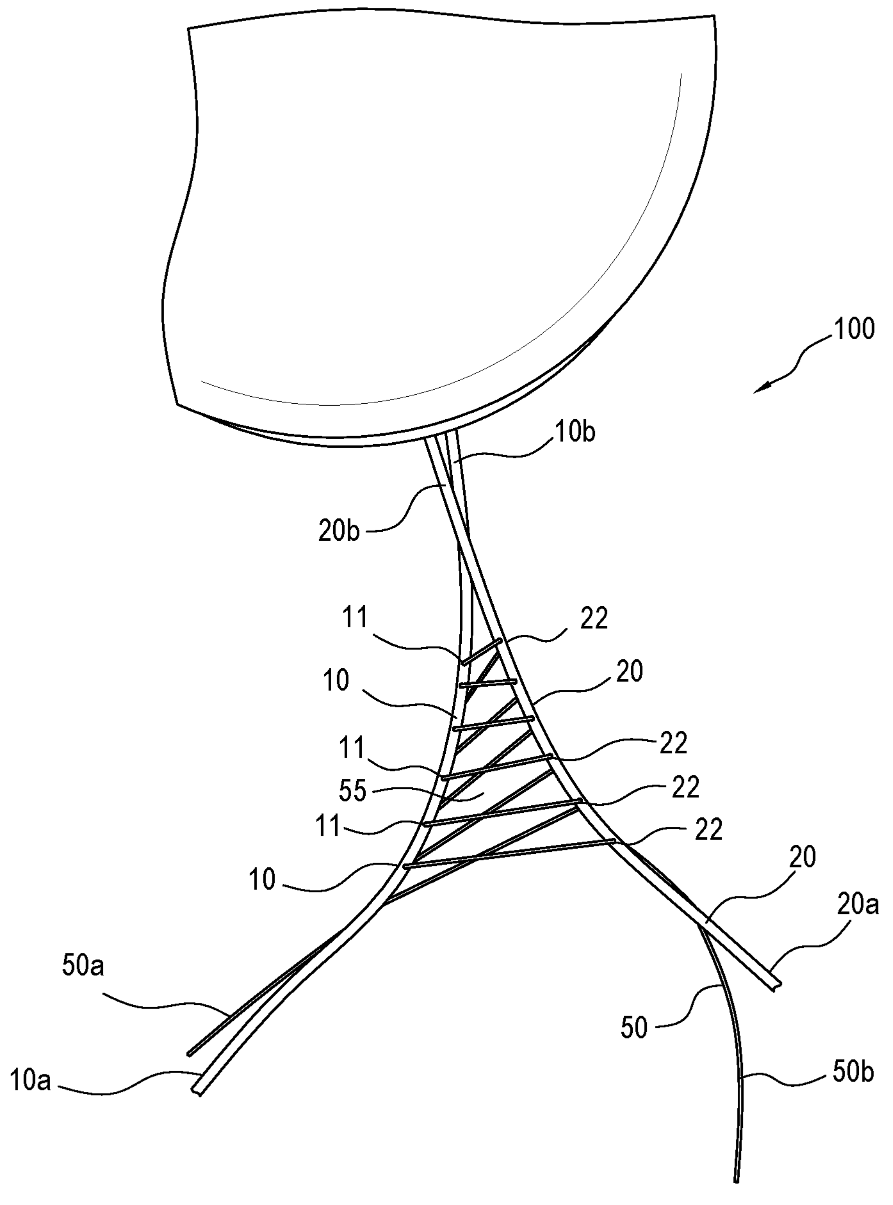
FIG. 2 illustrates another view of the surgical construct of FIG. 1.

Exemplary surgical construct 100 of FIGS. 1 and 2 is formed of two separate peripheral members 10, 20 (peripheral support members 10, 20; support members 10, 20; peripheral edges 10, 20; peripheral structures 10, 20; peripheral sutures or tapes 10, 20; rims 10, 20) coupled to flexible filament 50 (strand or coupler 50). Surgical construct 100 is a flexible, tensionable construct that may be knotted or knoteless.

Peripheral members 10, 20 may be formed of any flexible strands or materials known in the art such as suture, tapes, yarns, threads, fibers, ribbons, filaments, wires, textiles, meshes, non-metallic materials etc. The peripheral members 10, 20 may be flexible sutures made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). Peripheral members 10, 20 may be formed of tape such as suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Peripheral members 10, 20 may be also collagen tapes, or combination of Arthrex FiberTape® and collagen tapes.

Flexible filament 50 may be formed of any material that can be employed to form a web, a net, or a network with a pattern resembling that of a spiderweb or a web-like structure (such as a fishnet or loose mesh). Flexible filament 50 may be monofilament suture or including fibers of ultrahigh molecular weight polyethylene (UHMWPE) or the FiberWire® suture.

In the embodiment of FIGS. 1 and 2, and according to an exemplary embodiment, flexible filament 50 is threaded, weaved or interlaced through the members 10, 20 at various locations or points along longitudinal axis 15, 25 of the peripheral members 10, 20 (along the length of the peripheral members 10, 20). The threading locations where the filament penetrates the support member may be spaced apart from each other, at regular or irregular intervals. The locations may be also symmetrically or asymmetrically positioned relative to a longitudinal axis 55*a* of the web. FIG. 1 illustrates construct 100 in a first, straight, undeployed, unexpanded configuration wherein filament 50 is weaved through the peripheral members 10, 20 without forming any expanded web (only a small width/diameter interlacing). FIG. 2 illustrates surgical construct 100 in a second, deployed, expanded, spread configuration wherein filament 50 forms web 55 extending in between the peripheral members 10, 20 (with a larger width/diameter than the width/diameter of the interlacing). In the straight configuration of FIG. 1, surgical construct is inserted through small portals into a joint space, for example (and as detailed below) and then proximal limbs of the peripheral members 10, 20 are separated (pulled away from each other) to allow formation of web 55 over the area that needs to be approximated and/or fixated.

FIGS. 1 and 2 illustrate surgical construct 100 with a single filament 50 threaded through two peripheral members 10, 20 (first and second peripheral members 10, 20) at various points/locations along the lengths of the members 10, 20 to form web 55 (suture web 55; spreadable web 55; expandable web 55; spreadable central web 55; central webbing area 55; FiberWeb 55; net 55). Filament 50 is threaded through peripheral members 10, 20 at a plurality of first and second locations (for example, locations 11, 22) to form web 55 and two limbs 50*a*, 50*b* (loose ends 50*a*, 50*b*). Peripheral members 10, 20 may extend in a same direction and may be about parallel to each other and slightly spaced apart from each other (i.e., the second peripheral member 20 is slightly separate from the first peripheral member 10 and extends in a plane laterally spaced from the first peripheral member 10).

Filament 50 passes through the first peripheral member 10, extends to the second peripheral member 20, passes through the second peripheral member 20, back to the first peripheral member 10, passes through the first peripheral member 10 and then back to the second peripheral member 20 multiple times (a plurality of times) and at different locations along the first and second peripheral members 10, 20, creating at least one closed loop or a plurality of loops. The at least one loop extends between the first peripheral member 10 and the second peripheral member 20 and may be a closed and knotless loop. Filament 50 may form multiple loops when threaded through or passed around the two peripheral members 10, 20. In certain embodiments, filament 50 may pass once through at least one of the peripheral members at one or more locations. In certain embodiments, filament 50 may pass once through at least one of the peripheral members at one or more locations, and then looped around (wrapped around) at least one of the peripheral members. In certain embodiments, filament 50 may pass once through at least one of the peripheral members at one or more locations, and then secured to (or around) at least one of the peripheral members.

Pulling apart proximal ends 10*a*, 20*a* of peripheral members 10, 20 in the direction of arrow A (FIG. 1) spreads apart the members and forms web 55 which extends in between the spread-apart members, as shown in FIG. 2. In this embodiment, filament 50 is woven (threaded) through the peripheral members 10, 20 at locations 11, 22 without any fixed points or locations (i.e., filament 50 is able to slide through the peripheral members at any of locations 11, 22). During the surgical procedure, once the distal ends 10*b*, 20*b* of the construct are secured and fixated within a tissue, the proximal ends 10*a*, 20*a* of support members are separated to allow filament 50 to form web 55 with a general triangular configuration (FIG. 2) similar to that of a spiderweb. Web 55 is formed by pulling apart proximal ends 10*a*, 20*a* of the peripheral members 10, 20 to form the crisscross network or pattern of filament 50 and shorten the length of limbs 50*a*,

50*b*. The web 55 spreads over the tissue (or another tissue) and distal support members 10*a*, 20*a* are secured and fixated within the tissue (or another tissue). Limbs 50*a*, 50*b* at the proximal side of construct 100 can be pulled to allow the construct to narrow, i.e., to decrease the distance between the peripheral members 10, 20 (to achieve the straight configuration of FIG. 1).

The number of first locations 11 of first support member 10 may be equal to or different from the number of second locations 22 of second support member 20. The first locations 11 may extend along longitudinal axis 15 of first support member 10. The second locations 22 may extend along longitudinal axis 25 of second support member 20. The first and second locations 11, 22 may also extend towards the edges of peripheral members 10, 20 or combinations of middle and non-middle locations, i.e., off the longitudinal axis. Although FIG. 2 shows an embodiment with a plurality of first and second locations 11, 22, the present disclosure is not limited to this exemplary-only embodiment and contemplates filament 50 which is passed only once (one time) through at least one of the first and second support members 10, 20 at one or more locations. In certain embodiments, filament 50 may pass once through at least one of the first and second support members 10, 20 at one or more locations, and then looped around (wrapped around) at least one of the first and second support members 10, 20 and for once or more times. In certain embodiments, filament 50 may pass once through at least one of the first and second support members 10, 20 at one or more locations, and then secured to (or around) at least one of the first and second support members.

Figure 3:
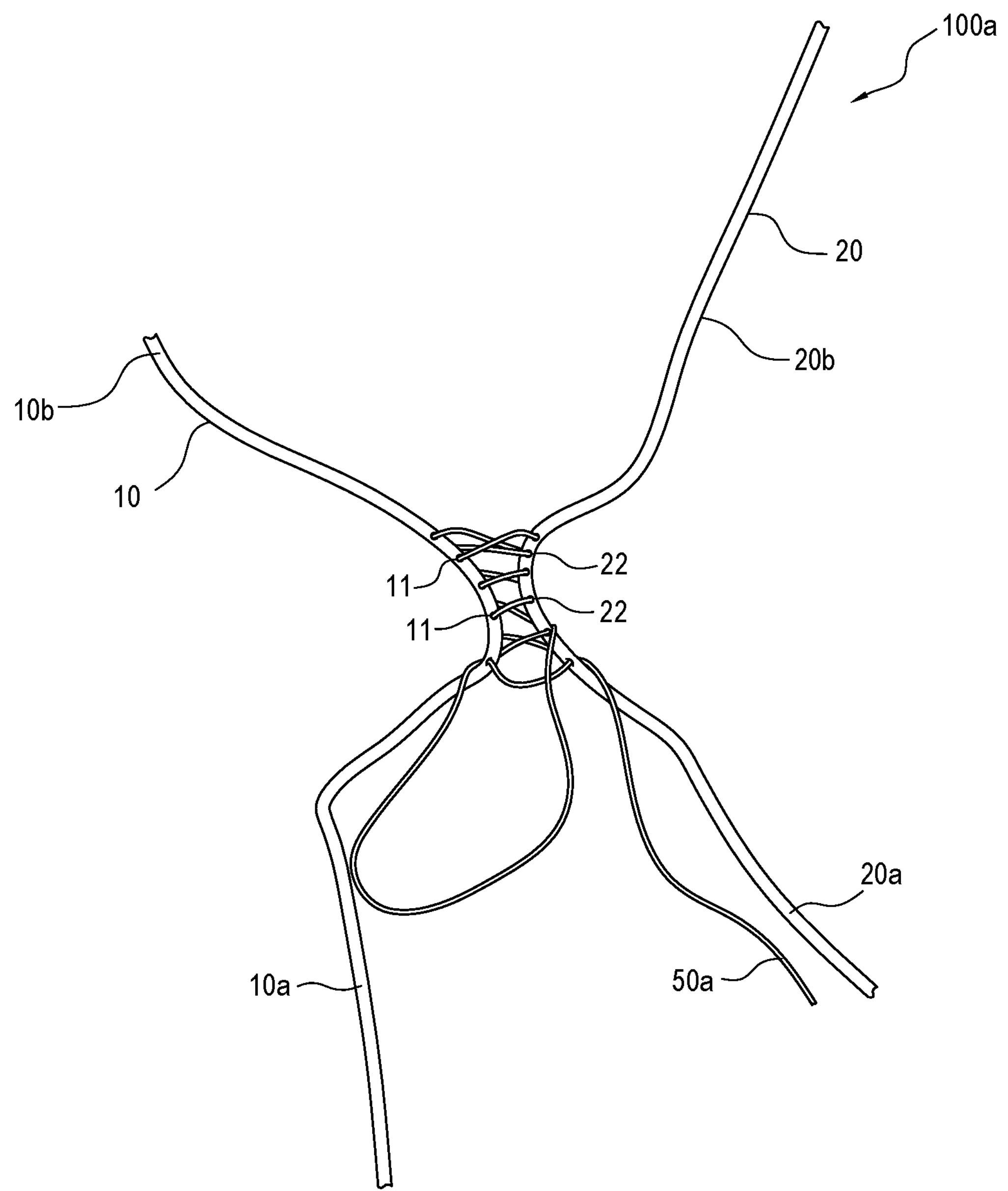
FIG. 3 illustrates another exemplary surgical construct.

FIG. 3 illustrates surgical construct 100*a* which is about similar to surgical construct 100 detailed above in that surgical construct 100*a* also includes two separate peripheral members 10, 20 coupled to filament 50, which is also threaded through the support members 10, 20 at different locations 11, 22. However, construct 100*a* is provided with only one proximal end 50*b* in lieu of two proximal ends.

FIGS. 4-11 illustrate exemplary surgical constructs 200, 200*a*, which are about similar to surgical constructs 100, 100*a* detailed above in that surgical constructs 200, 200*a* also include two separate peripheral members 10, 20. However, these constructs are provided with two flexible filaments 50, 60 that form web 155. Flexible filaments 50, 60 may be similar or different from each other, and may be formed of similar or different materials. Flexible filaments 50, 60 may be two suture strands, yarns, tapes or wires which may have similar or different characteristics, compositions, dimensions, properties, etc.

Figure 4:
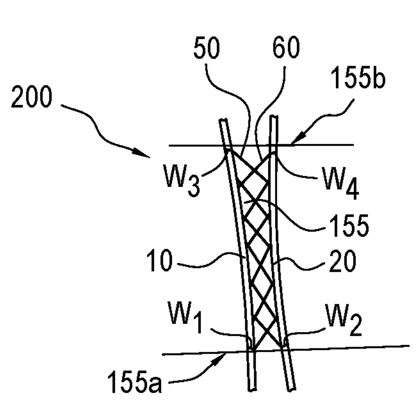
FIG. 4 illustrates another exemplary surgical construct.
Figure 5:
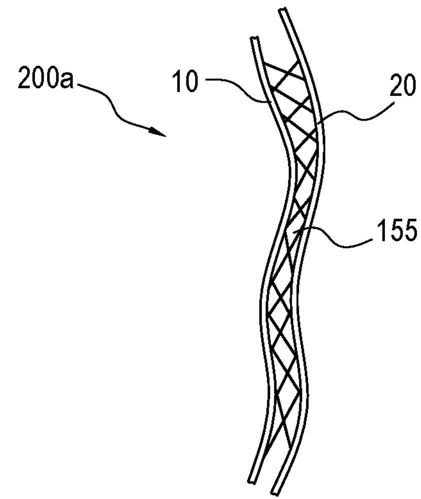
FIG. 5 illustrates another exemplary surgical construct.
Figure 6:
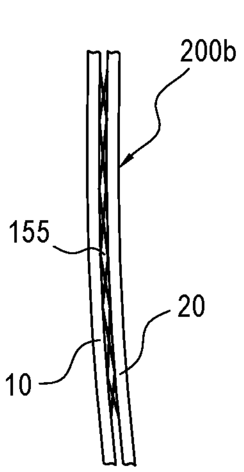
FIG. 6 illustrates another exemplary surgical construct.
Figure 7:
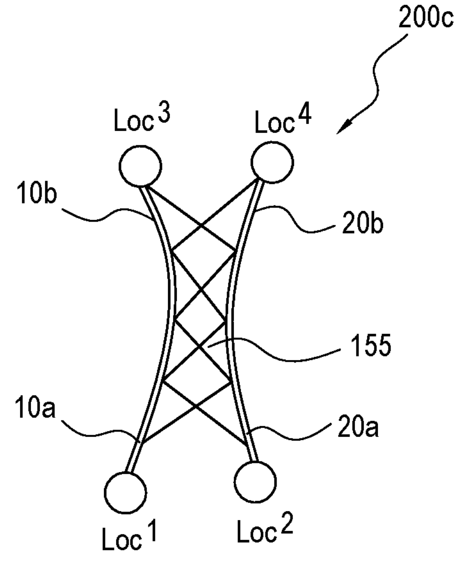
FIG. 7 illustrates another exemplary surgical construct.

FIG. 4 illustrates surgical construct 200 with two peripheral members 10, 20 extending about parallel to each other and with two filaments 50, 60 threaded through them and forming web 155. FIG. 5 illustrates surgical construct 200*a* having a more flexible configuration, with the two peripheral members 10, 20 extending about parallel to each other and with two filaments 50, 60 threaded through them and forming web 155. FIG. 6 illustrates surgical construct 200*b* in a first, unexpanded position with the two peripheral members 10, 20 also extending about parallel to each other and almost touching each other along their whole lengths, and with two filaments 50, 60 threaded through them in the first undeployed, unexpanded position. FIG. 7 illustrates surgical construct 200*c* with two filaments 50, 60 threaded through peripheral members 10, 20 and forming web 155 in a second, expanded configuration, with the four limbs 10*a*, 10*b*, 20*a*, 20*b* secured to tissue at four different locations Loc1, Loc2, Loc3, Loc4.

The filaments can be threaded through the peripheral members 10, 20 at a point, such as the midpoint, to prevent the web 155 from traveling. Filaments 50, 60 can be fixedly secured (affixed) to at least one of the members 10, 20 and to at least one location 11, 22, by knotting, gluing, splicing or similar methods known in the art. For example, surgical construct 200 of FIG. 4 may be formed of two filaments 50, 60 that are threaded through peripheral members 10, 20 at various locations 11, 22 and are fixed (securely fixed or affixed) at two most proximal web locations W1, W2 and two most distal locations W3, W4 by knotting or gluing, for example. In this embodiment, filaments 50, 60 may be formed of an elastic material (such as PEEK, for example) to allow web 155 to form when the peripheral members are spread apart. Web 155 is expandable and can be adjusted to various widths.

FIGS. 8-11 illustrate additional surgical construct 200*d* which is similar in part to constructs 200*a*, 200*b*, 200*c* above in that construct 200*d* also includes two peripheral members 10, 20 extending about parallel to each other and with two filaments 50, 60 forming web 155. However, filaments 50, 60 of construct 200*d* are not threaded through the peripheral members 10, 20 but are rather wrapped around each member 10, 20. In these embodiment, each filament 50, 60 ends in closed loops 51, 52 and 61, 62, respectively, formed around the members 10, 20. Loops 51, 52, 61, 62 are closed flexible loops with a diameter greater than the diameter (or width) of the peripheral members 10, 20 to allow sliding of the loops along the peripheral members to form the web. Loops 51, 52, 61, 62 may be closed knotless loops (formed by splicing, for example, or similar methods) or may be closed knotted loops.

Figure 8:
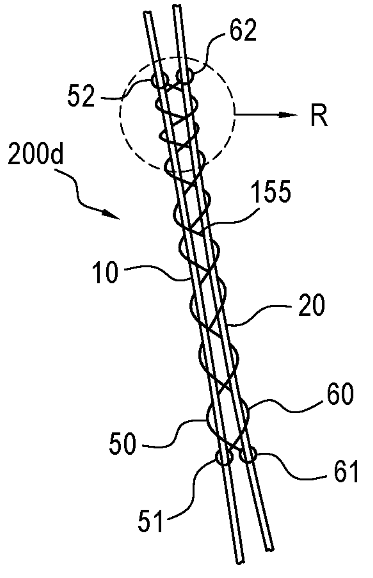
FIG. 8 illustrates another exemplary surgical construct.
Figure 9:
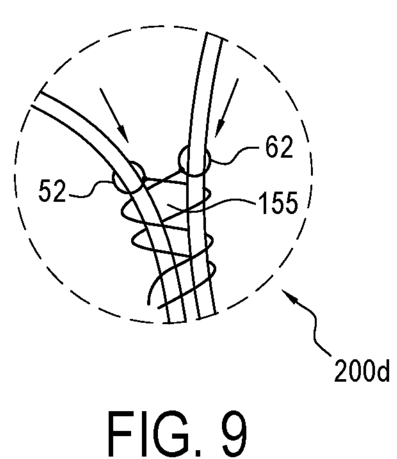
FIGS. 9-11 illustrate additional views of the surgical construct of FIG. 8.
Figure 10:
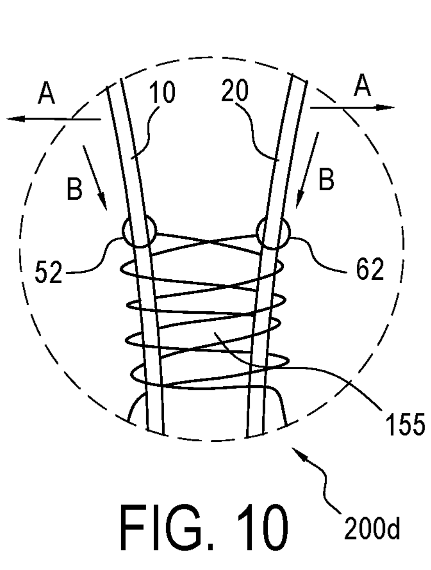
Figure 11:
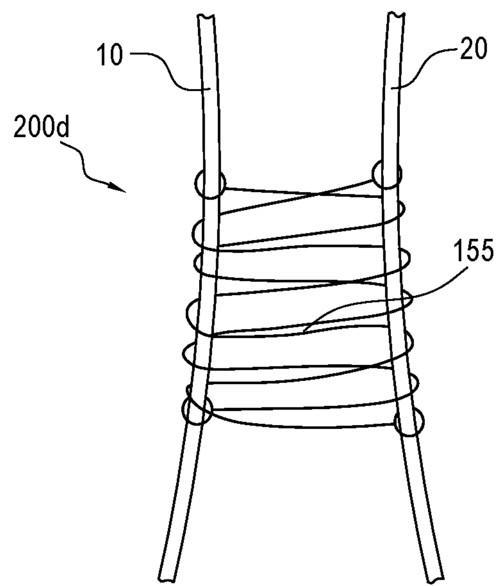

FIG. 8 illustrates construct 200*d* in the form of a slightly separated suture (formed of members 10, 20) with filaments 50, 60 looped around or wrapped around them. FIG. 9 is an enlarged view of area R of FIG. 8. FIG. 10 illustrates how the loops 52, 62 and web 155 travel in the direction of arrows B (sliding down the members 10, 20) when the suture 10, 20 is separated (i.e., when the members 10, 20 are spread apart in the direction of arrow A). The direction of arrows A is different from the direction of arrow B. In one exemplary embodiment, the direction of arrows A is about perpendicular to the direction of arrow B.

FIG. 12 illustrates another surgical construct 200*e* of the present disclosure which is about similar to construct 200 (detailed above) in that construct 200*e* also includes two peripheral members 10, 20 with two filaments 50, 60 forming web 155. However, filaments 50, 60 of construct 200*d* are not wrapped around each member 10, 20 but rather threaded through each member 10, 20. In this embodiment, each filament 50, 60 also ends in loops 51, 52 and 61, 62, respectively, formed around the members 10, 20. Filaments 50, 60 spread as they slide down the suture (10, 20) and as the sutures are separated. As filaments 50, 60 spread, the bunching creates resistance to further sliding.

FIG. 13 illustrates yet another embodiment of the present disclosure. Surgical construct 300 includes a single strand in the form of a suture or tape, for example, that furcates into multiple limbs. FIG. 13 shows only two exemplary limbs 10, 20 that are formed from bifurcating single strand/tape 30. One or more flexible filaments or strands are either threaded and/or looped around the peripheral members 10, 20 to form a spreadable web construct 255. For simplicity, FIG. 13 illustrates a single flexible filament 50 threaded through the limbs 10, 20 at various points and locations 11, 22 (as it was described above) and with a single fixed point P1 (a knot, for example).

Reference is now made to FIGS. 14 and 15 which illustrate schematic views of repairs 101, 102 with any of surgical constructs 100, 100*a*, 200, 200*a*, 200*b*, 200*c*, 200*d*, 200*e*, 300 of the present disclosure. Web 55, 155, 255 rests upon soft tissue and aids in the uniform compression of the tissue. Proximal and distal ends/limbs 10*a*, 10*b*, 20*a*, 20*b* of peripheral members 10, 20 are secured within tissue with various fixation devices 70 which may be knotted or knotless fixation devices. In an exemplary embodiment only, the fixation device 70 is a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein. An exemplary knotless fixation device 70 comprises an anchor body (or screw) and an eyelet.

Figure 16:
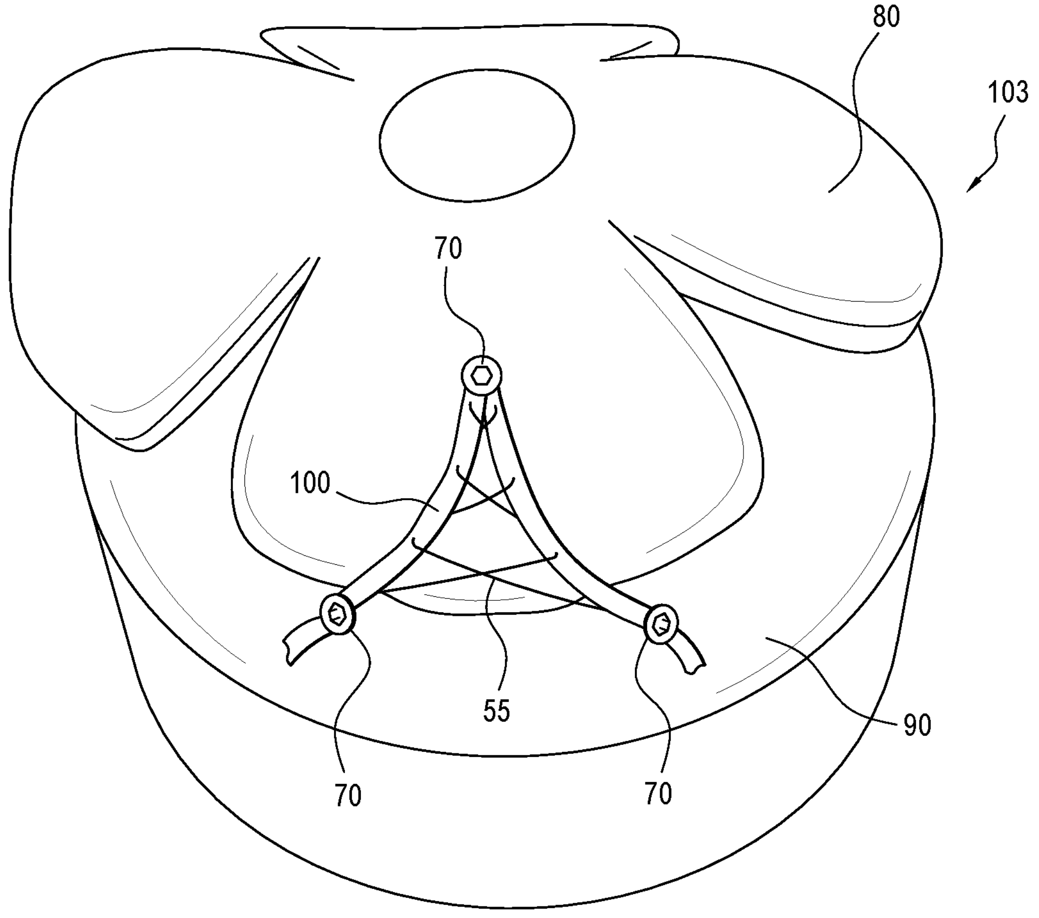
FIGS. 16 and 17 illustrate an exemplary knotless labral repair with the surgical construct of FIGS. 1 and 2.
Figure 17:
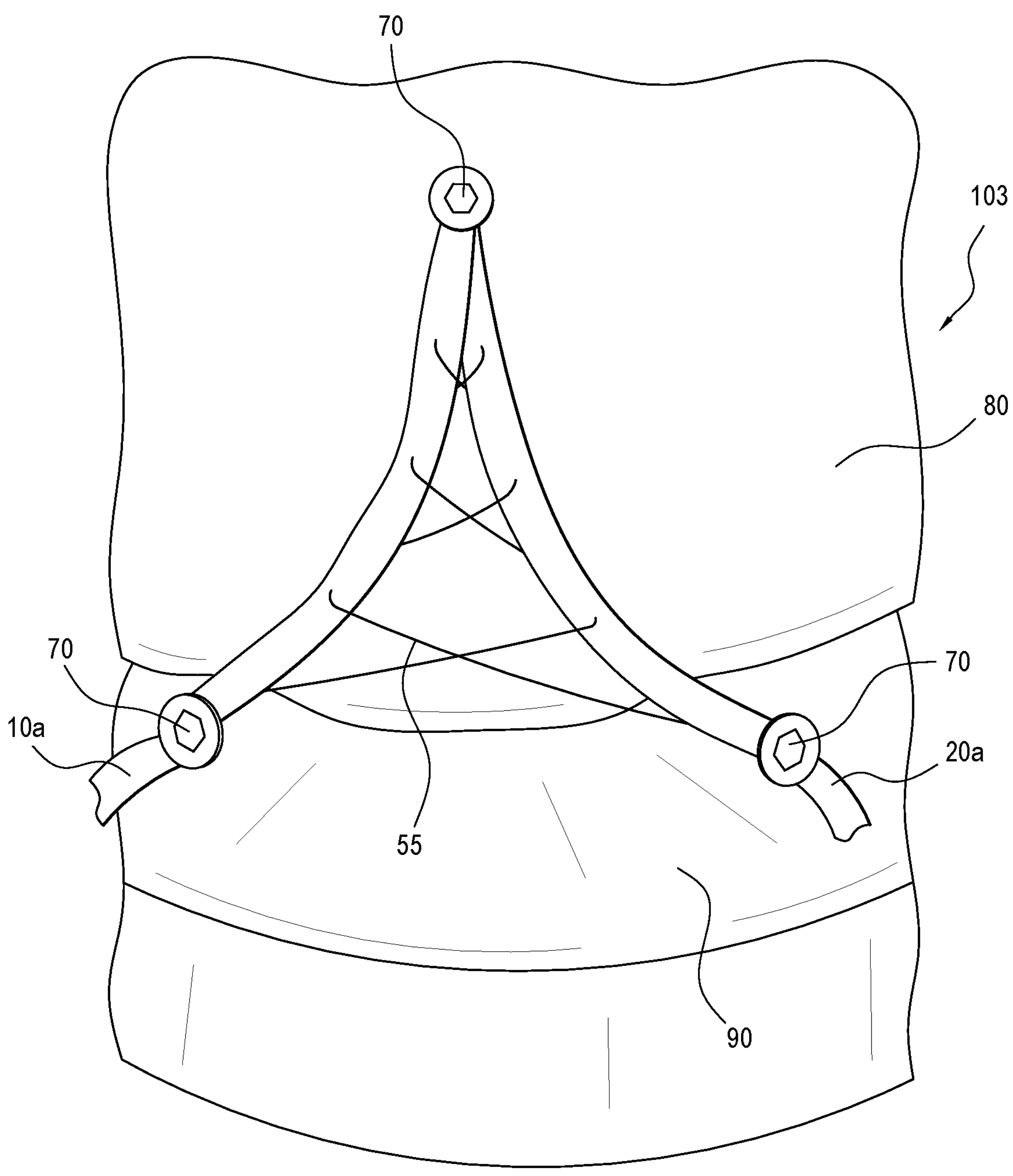

FIGS. 16 and 17 illustrate different views of a soft tissue repair 103 (arthroscopic rotator cuff repair) with exemplary surgical construct 100 of FIGS. 1 and 2. FIG. 16 illustrates a schematic view of a surgical site undergoing a method of fixation of first tissue to second tissue (soft tissue to bone, or soft tissue to soft tissue) by the methods of the present disclosure. In an exemplary embodiment only, the surgical site is the shoulder and the tissue is labrum 80 to be attached to glenoid 90 with surgical construct 100. Fixation devices 70 may be knotted or knotless fixation devices. Surgical construct 100 of the present disclosure may be provided pre-loaded (manufactured) on a fixation device (for example, a knotless fixation device such as device 70).

Fixation of soft tissue to bone, such as fixation of labrum to glenoid, typically involves the formation of an incision to access the surgical site and then reattachment of the soft tissue. When soft tissue is attached to bone, the surgeon drills a cavity in the bone and inserts a fixation device such as a bone anchor. FIGS. 16 and 17 illustrates repair 103 with three fixation devices 70, i.e., two lateral anchors 70 and one medial anchor 70 secured within bone 90. The medial anchor fixates limbs 10*b*, 20*b* of the peripheral members 10, 20. Each lateral anchor 70 fixates one of the proximal limbs 10*a*, 20*a* of the peripheral members. Medial and lateral anchors 70 may be exemplary knotless fixation devices provided with an eyelet (not shown) that allows limbs 10*a*, 20*a*, 10*b*, 20*b* to pass therethrough and additionally aid in the fixation of the labrum 80 to the glenoid 90. The limbs and web 55, 155, 255 pass across the soft tissue 80 and aid in its compression and fixation. The limbs 10*a*, 20*a* may be secured laterally by employing any number of fixation devices, knotless or otherwise, and the technique may be repeated multiple times at different locations in the bone.

FIGS. 18-35 illustrate additional exemplary constructs, assemblies, and repairs (FiberWeb applications) with surgical constructs 100, 100*a*, 200, 200*a*, 200*b*, 200*c*, 200*d*, 200*e*, 300, 300*a*, 300*b*, 300*c*.

Figures 18, 19, 20, 21:
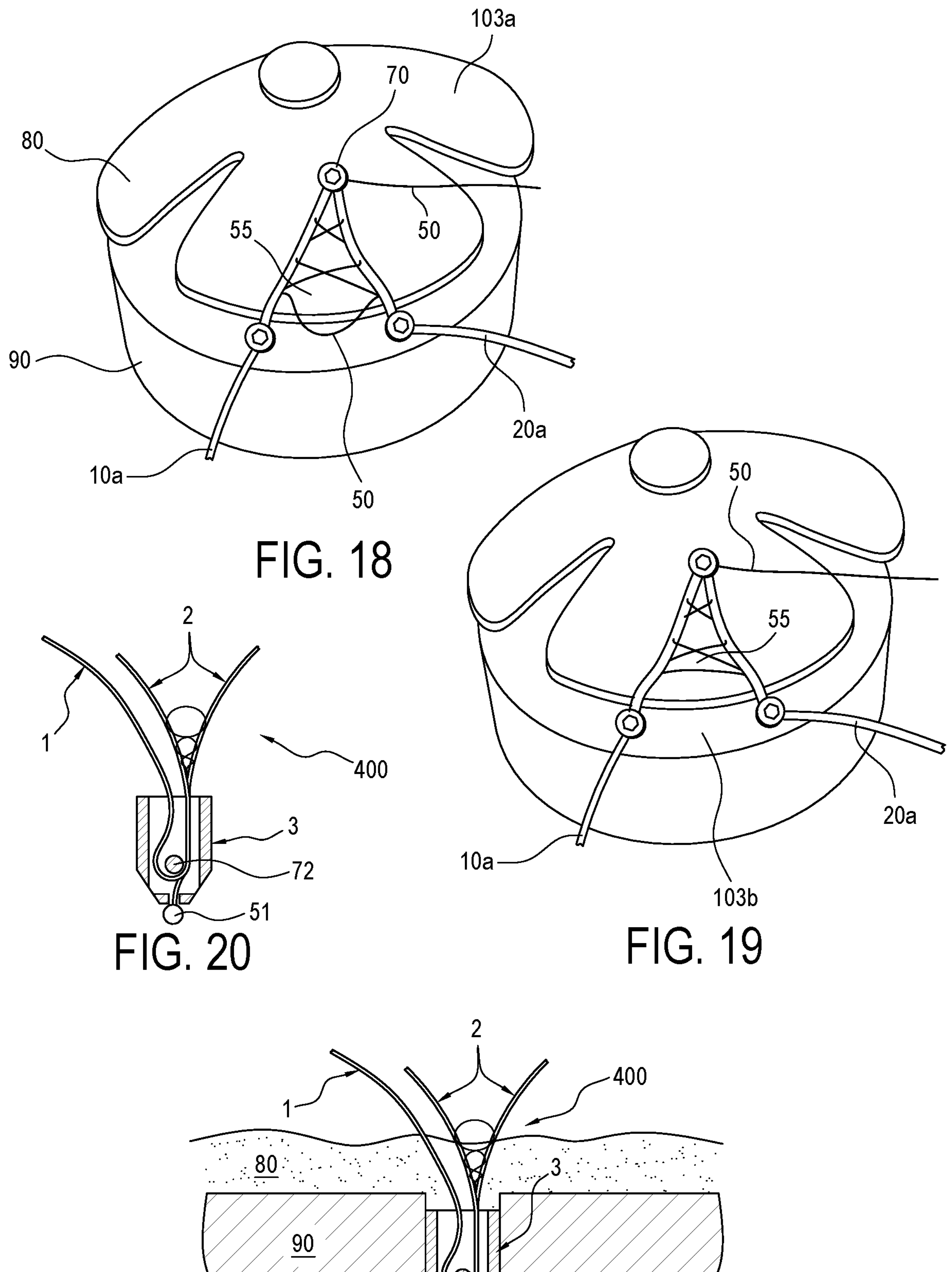
FIGS. 18 and 19 illustrate additional views of the knotless labral repair of FIGS. 16 and 17.
FIG. 20 illustrates a schematic view of a surgical assembly with the surgical construct of FIG. 18 and an exemplary knotless fixation device.
FIGS. 21-24 illustrate subsequent steps of an exemplary method of knotless repair with the surgical assembly of FIG. 20.

FIGS. 18 and 19 illustrate repairs 103*a*, 103*b* at intermediary stages of repair 103 of FIGS. 16 and 17, i.e., showing the tensioning of the construct prior to removal of limbs 10*a*, 20*a*, 50. FIG. 18 illustrates how the slack in suture 50 of repair 103*a* is removed and the suture is tightened down to pull the tissue 80 between the tape limbs down (FIG. 19). Pulling on suture 50 (web link 1) out of medial fixation device 70 allows tightening of the web 55 and of the overall final repair 103.

FIG. 20 illustrates details of an exemplary assembly 400 formed of an exemplary bone anchor 3 (fixation device 70) loaded with any of surgical constructs of the present disclosure such as surgical constructs 100, 100*a*, 200, 200*a*, 200*b*, 200*c*, 200*d*, 200*e*, 300. FIG. 21 illustrates assembly 400 of FIG. 20 inserted into bone 90 through tissue 80. Web 55, 155, 255 of the present disclosure is provided with repair suture limbs 2 (sutures 10, 20, 30) and web link 1 (filament 50, 60) forming the web between the two repair suture limbs 2. Bone anchor 3 (fixation device 70) may be a knotless anchor such as a knotless Corkscrew® anchor with a cinching mechanism with a post 72 that allows passing of the web link 1 through the anchor body and around the post 72 and formation of a knot 51, as detailed below. Bone anchor 3 (fixation device 70) may be a threaded or interference anchor.

Figures 22, 23, 24:
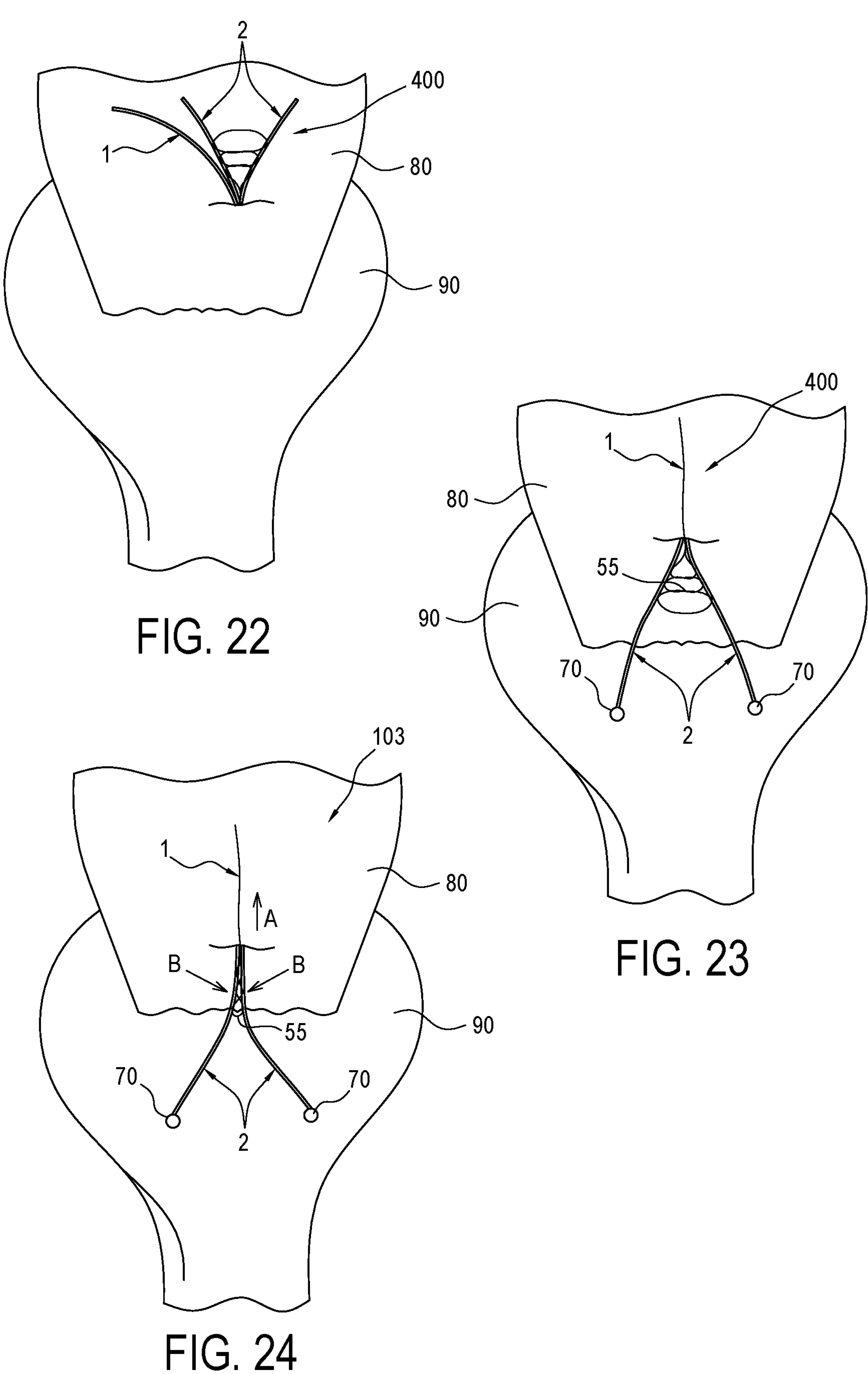

FIGS. 22-24 illustrate schematic views of surgical assembly 400 of FIGS. 20 and 21 undergoing a method of tissue repair with web link 1 (forming web 55, 155, 255) of the present disclosure. FIG. 22 shows assembly 400 installed into bone 90 through tissue 80. FIG. 23 illustrates suture limbs 2 passed over tissue 80 and secured into bone 90 with additional fixation devices 70 (such as anchor 3, for example). FIG. 24 shows how pulling on web link 1 of the FiberWeb 55 in the direction of arrow A allows tightening of the web construct extending between the two repair suture limbs 2 (in the direction of arrows B) and over the tissue 80 (securing the tissue 80 to bone 90) to obtain final repair 103. Tensioning occurs after all three fixation devices have been installed/secured into bone 90.

Figures 25, 26, 27:
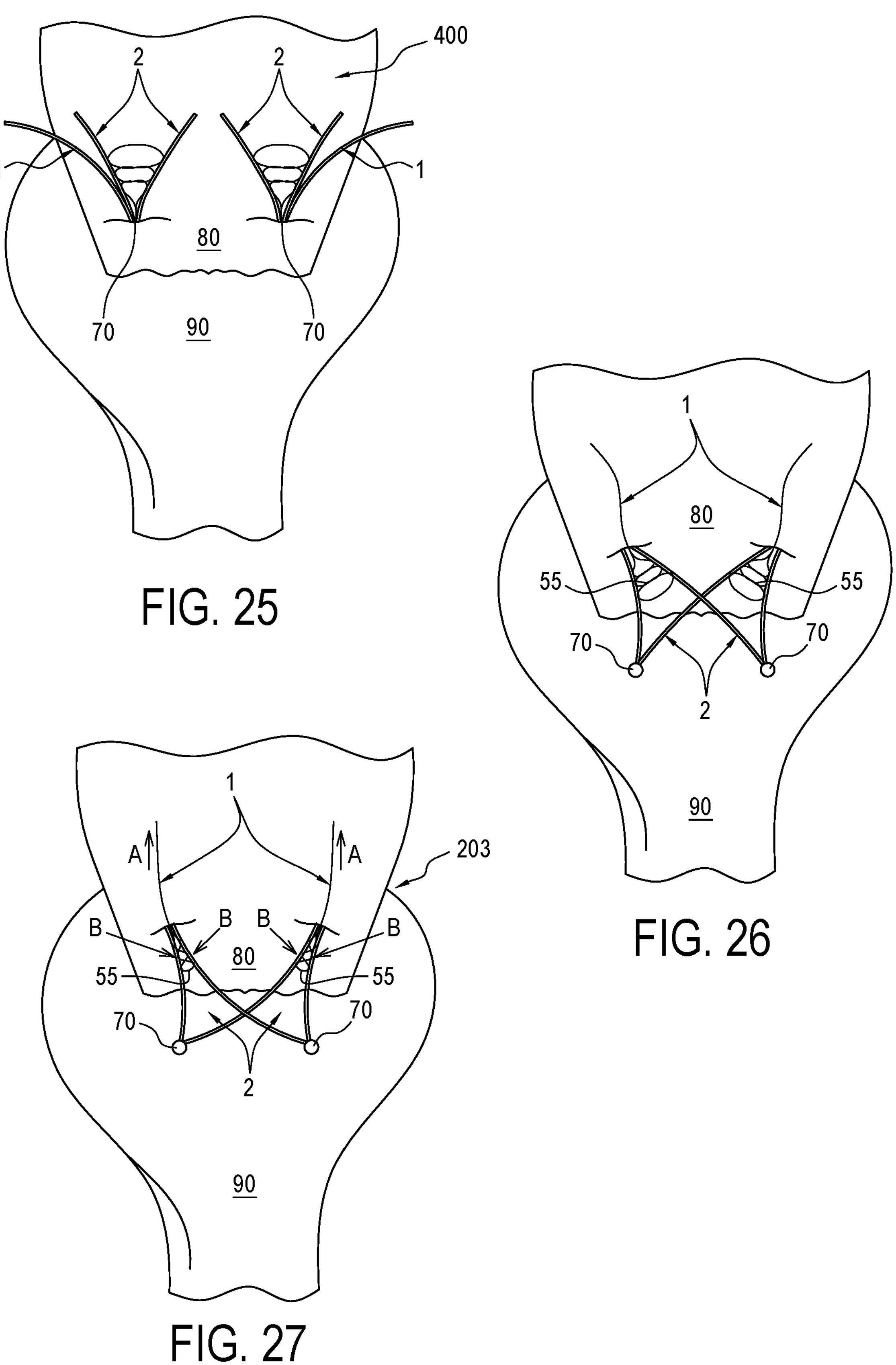
FIGS. 25-27 illustrate subsequent steps of another exemplary method of knotless repair with the surgical assembly of FIG. 20.

FIGS. 25-27 illustrate subsequent steps of tissue to bone repair 203 which is about similar to repair 103 detailed above but differs in the number of medial fixation devices, i.e., repair 203 includes two medial fixation devices 70 (bone anchors 3) instead of one medial fixation device as in repair 103. Suture limbs 2 from each medial anchor 70 (medial bone anchor 3) are passed over the tissue 80 and then secured into bone with separate distal fixation devices 70 (distal bone anchors 3) and at two separate locations, to form the criss-cross double row repair 203 (FIG. 27). Repair 203 may be any double row repair such as a knotless double row rotator cuff repair with a tensionable knotless web design suture that allows tensioning after the suture limbs/tapes have all been secured into bone. The construct is similar to the shoe laces on shoes except that they are knotless. Tensioning of repair 203 (FIG. 27) occurs only after all four fixation devices 70 have been installed/secured into bone 90.

For simplicity, repair 203 has been described with two FiberWebs 55, 155, 255 located over and in contact with soft tissue 80, i.e., with two medial fixation devices and two lateral distal fixation devices; however, the disclosure is not limited to this exemplary-only embodiment, and the disclosure also contemplates repairs with any number of webs and/or any number of medial and lateral fixation devices (hard body or soft body fixation devices).

Reference is now made to FIGS. 28-35 which depict additional exemplary embodiments of the FiberWeb concept of the present disclosure. Surgical construct 300*a* of FIG. 28 includes a single strand 30 in the form of a suture or tape, for example, that furcates into multiple limbs. Single strand 30 may be a braid. FIG. 28 shows bifurcated braid 30 with two limbs with filament 50 (web link 1) forming web 55. Only one end 50*a* of web link 1 (filament 50) exits the braid and is tensioned at the end of the repair.

Surgical construct 300*b* of FIG. 29 is similar to surgical construct 300*a* of FIG. 28 in that it also includes a single strand 30 in the form of a suture, braid or tape, for example, that bifurcates into two limbs forming web 55. However, surgical construct 300*b* has two tensioning ends 50*a*, 50*b* of web link 1 (filament 50) that exit the braid 30 and are tensioned at the end of the repair.

FIG. 30 illustrates surgical construct 300*c* which includes two button-holed sutures 31, 32 with web link 1 forming web 55 extending between the two button-holed sutures 31, 32. FIG. 31 illustrates assembly 500 which includes surgical construct 300*c* secured to (loaded onto) fixation device 70 (a threaded or interference anchor 70). Limb 50*b* and strands 31, 32 of surgical construct 300*c* may be securely attached to fixation device 70 by, for example, forming a knot such as single knot 51 (FIG. 31).

Sutures 31, 32 are provided with through-holes, openings, bifurcations, or eyelets 33 used for filament passing. Eyelets 33 are provided within the body of the material forming sutures 31, 32, at symmetrical or non-symmetrical positions. Eyelets 33 can have various dimensions as well as various forms and geometries, for example, round through-holes of about 1 mm each, and spaced apart from each other by about 2-4 mm, to allow a needle (or other suture passing instrument) with filament 50 to pass therethrough and aid in the web formation. Eyelets 33 can be reinforced around the perimeter of the holes/eyelets by threading around the opening, much like that of a button hole of a garment, to form reinforced eyelets 33. Eyelets 33 provided along the length of the suture 31, 32 (which may be flat suture tape 31, 32) permit for the shuttling of other filaments/sutures (flexible couplers or strands, such as filament 50 and any additional sutures) through the tape so as to provide "shuttling" eyelets. Eyelets 33 can also be used to attach additional strands of suture to permit additional compression of a suture construct created at a repair site. Eyelets 33 also facilitate improved healing at the repair site, permitting collagen ingrowth through the eyelets (or other growth/repair material through the eyelets).

FIGS. 32 and 33 illustrate surgical assembly 600, 700 with surgical construct 300*a*, 300*b* of FIGS. 28 and 29, respectively, secured to (loaded onto) fixation device 70 (threaded or interference anchor 70). Surgical assembly 600 is a single loaded Corkscrew® anchor. Surgical assembly 700 is a double loaded Corkscrew® anchor.

FIGS. 34 and 35 illustrate assembly 600*a*, 700*a* with surgical construct 300*a*, 300*b* of FIGS. 28 and 29, respectively, secured to (loaded onto) fixation device 70*a* which is a soft anchor and not a threaded or interference anchor (a Corkscrew® anchor). Soft suture anchors include a soft anchor sleeve or sheath (tubular member) with a body, a longitudinal axis, a first end and a second end, and a plurality of flexible strands extending through the body of the soft anchor sleeve or sheath.

Soft anchor 70*a* may be an "all-suture" anchor (soft suture anchor; all-suture soft knotless anchor) which is provided with a soft anchor sleeve (sheath or tubular member) with two open ends, and optional flexible shuttling strands extending through the soft anchor sleeve (sheath). The flexible strands may extend through the sleeve in similar or different directions and/or orientations and/or locations. The flexible tubular sleeve with the shuttling strands may be secured into or onto bone 90, and flexible strands may pass over soft tissue and are secured into bone to approximate soft tissue to bone. Details of an exemplary soft suture anchor with a soft anchor sleeve (sheath or tubular member) and flexible shuttling strands are set forth, for example, in U.S. application Ser. No. 15/998,516 entitled "Methods of Tissue Repairs" filed Aug. 16, 2018, the disclosure of which is incorporated by reference in its entirety herein.

Pulling on the filaments 50, 60 allows the tensioning of the web by decreasing the distance between the peripheral support places and/or increasing the tension of the web between those peripheral support places. The distance decreases in some fusing or approximating embodiments; however, a main function is increasing the tension to approximate tissue down (not horizontally but vertically), i.e., to approximate a first tissue to a second tissue in a more vertical direction.

The surgical constructs 100, 100*a*, 200, 200*a*, 200*b*, 200*c*, 200*d*, 200*e*, 300, 300*a*, 300*b*, 300*c* of the present disclosure may be also employed with knotted fixation devices, for example, knotted anchors. Thus, the disclosure is not limited to the use of surgical construct 100, 100*a*, 200, 200*a*, 200*b*, 200*c*, 200*d*, 200*e*, 300, 300*a*, 300*b*, 300*c* with only knotless fixation devices, and the disclosure contemplates the use of surgical constructs with any type of fixation device, knotless or knotted, or combination of knotless and knotted fixation devices.

In yet additional embodiments, surgical constructs 100, 100*a*, 200, 200*a*, 200*b*, 200*c*, 200*d*, 200*e*, 300, 300*a*, 300*b*, 300*c* may be employed with fixation devices which are in the form of soft anchors (soft suture anchors, or all-suture soft knotless anchors) provided with a soft anchor sleeve (sheath or tubular member) with two open ends, and at least two flexible shuttling strands extending through the soft anchor sleeve (sheath). The flexible strands may extend through the sleeve in similar or different directions and/or orientations and/or locations. The flexible tubular sleeve with the shuttling strands (attached to surgical construct 100, 100*a*, 200, 200*a*, 200*b*, 200*c*, 200*d*, 200*e*, 300, 300*a*, 300*b*, 300*c*) is secured into or onto bone, and the web 55, 155, 255 and tapes 10, 20 of the construct pass over soft tissue and are secured into bone to approximate soft tissue to bone.

A soft anchor may be provided pre-loaded onto the surgical construct 100, 100*a*, 200, 200*a*, 200*b*, 200*c*, 200*d*, 200*e*, 300, 300*a*, 300*b*, 300*c*, for example, with flexible strands threaded/passed through loops of filament 50, 60 and/or web 55, 155, 255. Fixation of tissue to bone is achieved by securing the sleeve of the soft anchor to a tip of a driver (not shown) and without requiring drilling of a bone hole or preparation of a pilot hole. The driver with surgical assembly (formed by the soft anchor and surgical construct 100, 100*a*, 200, 200*a*, 200*b*, 200*c*, 200*d*, 200*e*, 300, 300*a*, 300*b*, 300*c*) is passed through soft tissue 80 and bone 90 to fixate (install and secure) soft anchor within bone 90. Web area 55, 155, 255 and proximal limbs 10*a*, 20*a* of peripheral members 10, 20 remain outside the surgical site and positioned on a top surface of the soft tissue 80.

Surgical constructs 100, 100*a*, 200, 200*a*, 200*b*, 200*c*, 200*d*, 200*e*, 300, 300*a*, 300*b*, 300*c* detailed above have applicability to surgical procedures such as rotator cuff repair, Achilles tendon repair, patellar tendon repair, ACL/PCL reconstruction, hip and shoulder reconstruction procedures, and applications for suture used in or with suture anchors. In exemplary embodiments only, the surgical constructs 100, 100*a*, 200, 200*a*, 200*b*, 200*c*, 200*d*, 200*e*, 300, 300*a*, 300*b*, 300*c* of the present disclosure may be employed in tissue repairs that do not involve knot tying, for example, for use with suture anchors (such as PushLock® and/or SwiveLock® suture anchors and or Corkscrew® anchors) or for knotless arthroscopic suture repairs (such as knotless single row rotator cuff repair, or SpeedBridge™ repairs using no knots and only suture passing steps), among many others, all conducted with simplified steps as no additional instruments and passes are required.

Surgical constructs 100, 100*a*, 200, 200*a*, 200*b*, 200*c*, 200*d*, 200*e*, 300, 300*a*, 300*b*, 300*c* may be used in an exemplary SutureBridge™ tendon repair technique, developed by Arthrex, Inc., and disclosed in U.S. Pat. No. 8,012,174 (the disclosure of which is herein incorporated by reference in its entirety) which consists of a tied medial row constructed with two threaded suture anchors, combined with knotless lateral fixation using two Arthrex Push-Locks®. The construct enhances footprint compression and promotes tendon healing-to-bone with minimal knot tying.

Surgical constructs 100, 100*a*, 200, 200*a*, 200*b*, 200*c*, 200*d*, 200*e*, 300, 300*a*, 300*b*, 300*c* may be used in an exemplary SpeedBridge™ technique, also developed by Arthrex, Inc., and disclosed in U.S. Pat. No. 9,005,246 (the entire disclosure of which is herein incorporated by reference) which uses a threaded swivel anchor combined with FiberTape® to create a quick and secure SutureBridge™ construct with no knots and only two suture passing steps. In the SpeedBridge™ technique, a swivel anchor, preferably an Arthrex 4.75 mm SwiveLock® C, loaded with one strand of FiberTape®, is inserted into a medial bone socket. A suture shuttle such as FiberLink™ may be used to shuttle both FiberTape® tails through the rotator cuff simultaneously. A FiberLink™ tail is passed through the rotator cuff using a suture passing instrument such as the Scorpion™. The tails of the FiberTape® are loaded through the FiberLink™ loop and shuttled through the rotator cuff. These steps are repeated for the second medial row anchor.

Surgical constructs 100, 100*a*, 200, 200*a*, 200*b*, 200*c*, 200*d*, 200*e*, 300, 300*a*, 300*b*, 300*c* may be employed in a method of double row fixation of tendon to bone, as detailed in U.S. Pat. No. 8,012,174. An exemplary tissue fixation comprises inter alia the steps of: (i) attaching surgical construct 100, 100*a*, 200, 200*a*, 200*b*, 200*c*, 200*d*, 200*e*, 300, 300*a*, 300*b*, 300*c* to a fixation device 70 (for example, a knotless fixation device or a soft anchor); (ii) securing the fixation device 70 into bone while the construct is positioned over soft tissue 80; (iii) separating proximal limbs of peripheral members 10, 20, 30 to form web 55, 155, 255 over the soft tissue 80 to be repaired; and (iv) securing at least one of the proximal limbs of the peripheral members 10, 20, 30 into bone 90. The method may further comprise the step of securing the fixation device into a bone socket or tunnel, or pushing the fixation device into bone without forming a bone socket or tunnel.

Peripheral members 10, 20, 30 may be formed of any flexible strands or materials known in the art such as suture, tapes, yarns, threads, fibers, ribbons, filaments, wires, textiles, meshes, non-metallic materials etc. The peripheral members 10, 20, 30 of the surgical construct 100, 100*a*, 200, 200*a*, 200*b*, 200*c*, 200*d*, 200*e*, 300, 300*a*, 300*b*, 300*c* provide reinforcement, holding and support, as well as equally-distributed compression, of first tissue (for example, soft tissue such as tendon or ligament) to be attached to second tissue (for example, bone).

Peripheral members 10, 20, 30 may be flexible sutures made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). Peripheral members 10, 20, 30 may be formed of suture tape, for example, Arthrex FiberTape®, which is a high strength suture tape that is braided and rectangular-like in cross section and as disclosed in U.S. 7,892,256, the disclosure of which is incorporated by reference in its entirety herein. Peripheral members 10, 20, 30 may be also collagen tapes, or combination of Arthrex FiberTape® and collagen tapes.

Filaments 50, 60 may be any type of flexible material or suture known in the art or any material that can be employed to form a web or structure resembling a spiderweb. Filaments 50, 60 may be monofilament suture or including fibers of ultrahigh molecular weight polyethylene (UHMWPE) or the FiberWire® suture (disclosed in U.S. Pat. No. 6,716,234, the disclosure of which is hereby incorporated by reference in its entirety herein).

Filaments 50, 60 may be threaded or weaved through the support members 10, 20, 30 at various locations or points along the longitudinal axis (along the length) of the support members 10, 20, 30. The threading locations where the filament penetrates the support member may be spaced apart from each other at regular (or irregular) intervals. The locations may be also symmetrically or asymmetrically positioned relative to a longitudinal axis of the web. The end locations of the webbing area (defined by the two most distal and two most proximal threading locations on the support members) may be securely affixed or fixed to the support members (by forming a knot, for example) or may be movable or partially movable with respect to the members 10, 20, 30 (and secured to additional devices).

Filaments 50, 60 may be looped around (wrapped around) the support members 10, 20, 30 instead of being threaded through the support members 10, 20, 30. In these embodiments, the filaments at the proximal end locations defining the webbing area may terminate in loops that can slide down the support member (i.e., could travel along its length). When the proximal ends of the two support members are separated (by pulling them apart, for example), the inter-webbing spreads out over the area to be fixated and/or compressed and/or approximated. Fixation of the web may be conducted with additional fixation devices such as additional anchors.

The peripheral members 10, 20, 30 and filaments 50, 60 of the present disclosure may be also formed of a stiff material, or combination of stiff and flexible materials, depending on the intended application. The peripheral members 10, 20, 30 and filaments 50, 60 may be also coated and/or provided in different colors. The peripheral members 10, 20, 30 and filaments 50, 60 may be also provided with tinted tracing strands, or otherwise contrast visually with the remaining elements of the construct, which could be a plain, solid color, or display a different tracing pattern, for example. Various structural elements of surgical construct 100, 100*a*, 200, 200*a*, 200*b*, 200*c*, 200*d*, 200*e*, 300, 300*a*, 300*b*, 300*c* may be visually coded, making identification and handling of the suture legs and filaments simpler. Easy identification of suture in situ is advantageous in surgical procedures, particularly during arthroscopic surgeries, such as endoscopy and laparoscopy.

The surgical construct 100, 100*a*, 200, 200*a*, 200*b*, 200*c*, 200*d*, 200*e*, 300, 300*a*, 300*b*, 300*c* may include surgical sutures or similar materials that may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

Surgical constructs, assemblies and methods of tissue repairs are disclosed. A surgical construct 100, 100*a*, 200, 200*a*, 200*b*, 200*c*, 200*d*, 200*e*, 300, 300*a*, 300*b*, 300*c* includes a spreadable web 55, 155, 255 attached to a plurality of peripheral strands or members 10, 20, 30. The spreadable web 55, 155, 255 may be tensionable and may include one or more flexible filaments or strands. At least one of the filaments is coupled to the peripheral members.

The spreadable web 55, 155, 255 may be knotless. The spreadable web 55, 155, 255 may be tensionable.

Surgical construct 100, 100*a*, 200, 200*a*, 200*b*, 200*c*, 200*d*, 200*e*, 300, 300*a*, 300*b*, 300*c* may be a flexible knotless anchor employed for fixation of tissue. The surgical construct 100, 100*a*, 200, 200*a*, 200*b*, 200*c*, 200*d*, 200*e*, 300, 300*a*, 300*b*, 300*c* may be attached to one or more knotless fixation devices 70. The surgical construct 100, 100*a*, 200, 200*a*, 200*b*, 200*c*, 200*d*, 200*e*, 300, 300*a*, 300*b*, 300*c* may be employed in knotted or knotless fixation of first tissue 80 to second tissue 90, for example, fixation of soft tissue 80 (ligament, tendon, etc.) to bone 90.

A surgical construct 100, 100*a*, 200, 200*a*, 200*b*, 200*c*, 200*d*, 200*e*, 300 may consist essentially of two separate peripheral pieces or support members having two proximal limbs, two distal limbs and a spreadable suture web extending between the two peripheral pieces or support members. The spreadable suture web may be a central web.

A surgical construct 100, 100*a*, 200, 200*a*, 200*b*, 200*c*, 200*d*, 200*e*, 300, 300*a*, 300*b*, 300*c* includes a central webbing area in the form of an expandable suture web positioned between two peripheral strands such as two suture tapes. The surgical construct may be provided as a "one piece" construct (with the filament(s) already coupled to the peripheral strands) or may be assembled in situ. The construct eliminates the knot formation in surgical tissue repairs and increases tissue compression due to the spread web.

The present disclosure also provides a surgical assembly which includes a fixation device 70 coupled with a surgical construct 100, 100*a*, 200, 200*a*, 200*b*, 200*c*, 200*d*, 200*e*, 300, 300*a*, 300*b*, 300*c* formed of a web 55, 155, 255 with at least three limbs of members 10, 20, 30 extending away from the web.

Methods of tissue repairs are also disclosed. The repairs may be knotted or knotless. In one embodiment, surgical constructs 100, 100*a*, 200, 200*a*, 200*b*, 200*c*, 200*d*, 200*e*, 300, 300*a*, 300*b*, 300*c* provide knotless bridge soft tissue to bone fixation, without any knot formation, with fewer passing steps, improved handling through small portals and into the joint space, and with increased fixation and soft tissue compression.

An exemplary method of tissue repair may comprise inter alia the steps of: (i) securing a surgical construct 100, 100*a*, 200, 200*a*, 200*b*, 200*c*, 200*d*, 200*e*, 300, 300*a*, 300*b*, 300*c* in the form of a spreadable web 55, 155, 255 with sutures 10, 20, 30 to a first tissue 90; and (ii) positioning the spreadable web 55, 155, 255 over a second tissue 80 and securing the surgical construct to the second tissue. The construct includes slightly separated sutures 10, 20, 30 with one or more filaments 50, 60 weaved through or looped around at various points to form the web. The construct may be secured to first and second tissues with fixation devices 70. Fixation devices 70 may be any of (1) knotless fixation devices such as a swivel anchor or a pushlock anchor; (2) knotted fixation devices; or (3) soft suture anchors which include a soft anchor sleeve or sheath with a body, a longitudinal axis, a first end and a second end, and a plurality of flexible strands extending through the body of the soft anchor sleeve or sheath; or (4) any combinations thereof.

A tensionable spreadable FiberWeb construct includes a plurality of peripheral members 10, 20, 30 (such as sutures or tapes) extending generally in a first direction and at least one filament 50, 60 (such as monofilament suture) extending generally in a second direction. The first direction may be different from the second direction. The first direction may be perpendicular to the second direction. The at least one filament 50, 60 is coupled to the plurality of peripheral members 10, 20. In one embodiment, at least one filament 50, 60 is threaded through the plurality of strands at various points 11, 22 (such as in the central webbing area or at the end points om the strands) as long as the filament 50, 60 does not interfere with the expansion of the web 55, 155, 255. In one embodiment, multiple filaments 50, 60 are threaded through the plurality of strands. The multiple filaments 50, 60 may be completely separated from each other and/or connected to one (or some or all) filament at different points and locations. In one embodiment, at least one filament 50, 60 is looped around the strands 10, 20, 30. In one embodiment, all filaments 50, 60 are looped around the strands 10, 20, 30.

The tensionable spreadable web construct of the present disclosure has a small initial diameter and it spreads when the sutures are separated. When the user pulls the sutures apart, the filament threaded/weaved through the sutures expands the width of the web forming a spreadable suture web. The construct includes slightly separated suture(s) with a filament weaved through at various points. In one embodiment, filaments spread as they slide down the suture and as the sutures are separated. As filaments spread, the bunching creates resistance to further sliding. Filament can be threaded through the suture at a point, such as the midpoint, to prevent the web from traveling.

The suture can have a filament threaded through at various points such as in the central webbing area or at the end points, as long as it does not interfere with the expansion of the web. The construct may have multiple configurations. Tendon passing and trans tendon are feasible and compression over soft tissue is increased and uniform.

The present disclosure also provides an apparatus with a fixed point which does the webbing on one end and the slide-able as it goes down the tape. That allows the spreading to stretch the web.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of tissue repair comprising the steps of:

inserting through a portal into a joint space a surgical construct formed of a single filament extending between and coupling at least two peripheral support structures, wherein the single filament passes through or around each of the at least two peripheral support structures at least once and at multiple locations;

securing a first tissue to a second tissue with the surgical construct and with a plurality of fixation devices by securing the surgical construct to one of the plurality of fixation devices and installing the one of the plurality of fixation devices into the first tissue;

separating proximal limbs of the at least two peripheral support structures to form a tensionable, spreadable suture web, the tensionable, spreadable suture web being expandable and adjustable to various widths;

subsequently, adjusting a width of the tensionable, spreadable suture web to correspond to a width of area to be covered of the second tissue;

spreading the tensionable, spreadable suture web over the area to be covered of the second tissue to fixate and uniformly compress the second tissue;

securing each of the at least two peripheral support structures to other of the plurality of fixation devices and installing the other of the plurality of fixation devices with the at least two peripheral support structures into or onto the second tissue;

and tensioning the tensionable, spreadable suture web and the tissue repair subsequent to securing the plurality of fixation devices within the first tissue and the second tissue.

2. The method of claim 1, wherein the step of tensioning the tensionable, spreadable suture web includes pulling on the single filament coupled to the at least two peripheral support structures of the tensionable, spreadable suture web, to approximate the first tissue to the second tissue.

3. The method of claim 1, wherein the step of securing the first tissue to the second tissue comprises the steps of:

passing the at least two peripheral support structures over the second tissue; and pulling on the at least two peripheral support structures to separate them and to spread the tensionable, spreadable suture web over the second tissue.

4. The method of claim 1, wherein the step of securing the each of the at least two peripheral support structures to the other of the plurality of fixation devices further comprises threading each of the at least two peripheral support structures through apertures or eyelets of the other of the plurality of fixation devices.

5. The method of claim 1, wherein at least one of the plurality of fixation devices is an all suture soft anchor.

6. The method of claim 1, wherein at least one of the plurality of fixation devices is a hard body anchor.

7. The method of claim 1, wherein the first tissue is bone and the second tissue is soft tissue.

8. The method of claim 1, wherein the tensionable, spreadable suture web includes the single filament coupled two peripheral support structures, wherein the two peripheral support structures are sutures or suture tapes.

9. The method of claim 1, wherein the suture web has a triangular configuration.

10. The method of claim 1, wherein the tissue repair is rotator cuff repair.

11. The method of claim 1, wherein the tissue repair is a knotless tissue repair.

12. A method of knotless tissue repair comprising the steps of:

connecting a plurality of fixation devices to a tensionable surgical web formed by passing at least one filament through or around a first peripheral strand and through or around a second peripheral strand, wherein the tensionable surgical web has a triangular configuration;

installing the plurality of fixation devices into hard tissue;

positioning the tensionable surgical web over soft tissue to be secured to the hard tissue; and subsequently, tensioning the tensionable surgical web to secure the soft tissue to the hard tissue by pulling on the at least one filament of the tensionable surgical web to decrease a width of the tensionable surgical web.

13. The method of claim 12, wherein the plurality of fixation devices are knotless anchors or knotless soft suture anchors, or combinations thereof.

14. The method of claim 12, wherein the step of installing the plurality of fixation devices comprises securing each of the plurality of fixation devices into the hard tissue before the step of tensioning the tensionable surgical web.

15. A method of tissue repair comprising the steps of:

inserting through a portal into a joint space a surgical construct, wherein the surgical construct is formed of a filament and a single strand furcated into at least two peripheral limbs, wherein the filament extends between and couples the at least two peripheral limbs by passing through or around each of the at least two peripheral limbs at least once and at multiple locations;

securing the single strand to a knotless fixation device and installing the knotless fixation device into bone;

separating and pulling apart the at least two peripheral limbs to form a spreadable, tensionable web with a triangular configuration;

spreading the spreadable, tensionable web over soft tissue to be attached to the bone;

securing each of the at least two peripheral limbs to additional fixation devices; and subsequently, tensioning the spreadable, tensionable web to fixate and uniformly compress the soft tissue.

16. The method of claim 15, wherein the filament is suture, and the single strand is suture or tape.

* * * * *